(12) United States Patent
Harbison et al.

(10) Patent No.: US 9,192,401 B2
(45) Date of Patent: Nov. 24, 2015

(54) DUAL-PLANE FEMORAL GUIDE ASSEMBLY

(71) Applicant: Biomet Sports Medicine, LLC, Warsaw, IN (US)

(72) Inventors: Kyle Harbison, Winona Lake, IN (US); Jason Meridew, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 245 days.

(21) Appl. No.: 14/018,973

(22) Filed: Sep. 5, 2013

(65) Prior Publication Data

US 2015/0066040 A1 Mar. 5, 2015

(51) Int. Cl.
*A61B 17/04* (2006.01)
*A61B 17/17* (2006.01)

(52) U.S. Cl.
CPC ......... *A61B 17/1764* (2013.01); *A61B 17/1714* (2013.01)

(58) Field of Classification Search
USPC ............................................. 606/96–98, 148
See application file for complete search history.

(56) References Cited

U.S. PATENT DOCUMENTS

2012/0265205 A1 * 10/2012 Steiner et al. .................... 606/80

OTHER PUBLICATIONS

Asheesh Bedi, MD, Answorth Allen, MD and David W. Altchek, MD, Smith & Nephew, Inc., "Anatomic ACL Reconstruction Using the Clancy Flexible Drill Guide System", pp. 1-10, Andover, MA, Apr. 2012.
Cayenne Medical, "The AperFix System AM Portal Surgical Technique Guide", Scottsdale, Arizona, http://cayennemedical.com/wordpress/wp-content/uploads/11262-D-AM-Portal-Technique.pdf.
Charles H. Brown Jr., MD and Tim Spalding, MD, Smith & Nephew, Inc., "Knee-Technique Guide, Single Bundle ACL Reconstruction Medial Portal Technique", pp. 1-19, Andover, MA, Apr. 2012.
Smith & Nephew, Inc. "Clancy Anatomic Cruciate Guide", Andover, MA, Mar. 2012.
Stryker Corporation, "Versitomic Flexible Reaming System", Mahwah, NJ, Nov. 2010.
Stryker Corporation, "Versitomic Flexible Reamer System", Mahwah, NJ, Feb. 2010.
Smith & Nephew, "Clancy Flexible Drill Guide System Anatomic ACL Reconstruction, Knee Series Technique Guide by: Asheesh Bedi, MD, Answorth Allen, MD, and David Altchek, MD", pp. 1-10, Andover, MA, Aug. 2010.
Smith & Nephew, "Knee Technique Guide Anatomical ACL Reconstruction Using the Clancy Flexible Drill System by Asheesh Bedi, MD, Answorth Allen, MD, and David W. Altchek, MD", pp. 1-9, Andover, MA, Apr. 2012.
Smith & Nephew, "Anatomic ACL Reconstruction Using the Clancy Anatomic Cruciate Guide/Flexible Drill System", Join Intelligence, Issue 2, vol. 1, Nov. 2009.

* cited by examiner

*Primary Examiner* — Sameh Boles
(74) *Attorney, Agent, or Firm* — Schwegman Lundberg & Woessner, P.A.

(57) ABSTRACT

A guide assembly for use in preparing a femur for soft tissue reconstruction is provided. The guide assembly can include a guide shaft member that can extend from a proximal end to a distal end thereof and can include a distal region encompassing the distal end. The distal region can have a first bend in a first direction and a second bend in a second direction different than the first direction.

23 Claims, 9 Drawing Sheets

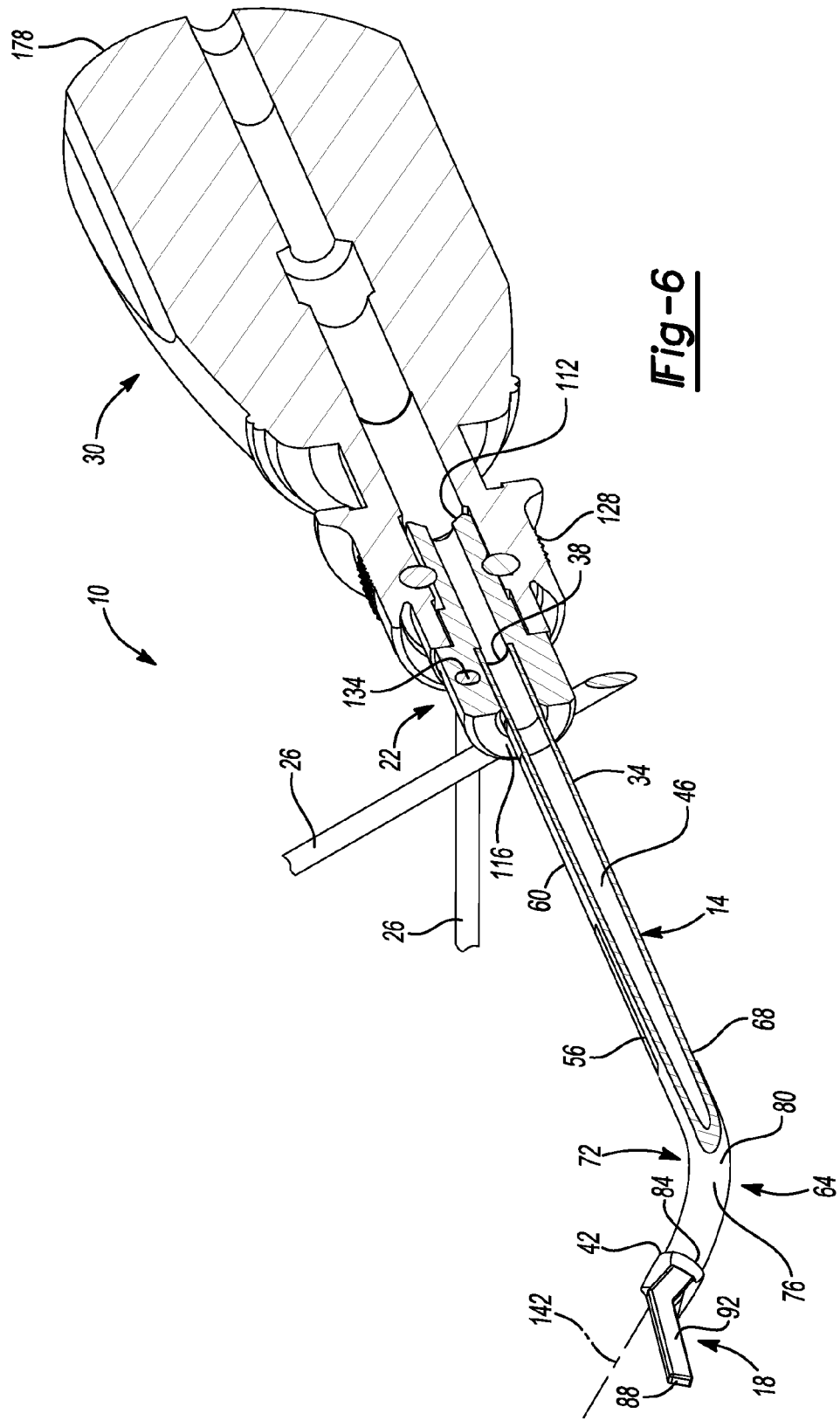

DUAL-PLANE FEMORAL GUIDE ASSEMBLY

FIELD

The present disclosure relates generally to instrumentation for reconstruction of soft tissue and, more particularly, to a dual-plane femoral guide assembly for reconstruction of soft tissue, such as tendons and ligaments.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Current surgical procedures for reconstruction of the anterior cruciate ligament (ACL) can include reconstructing the torn or otherwise injured ACL with a ligament graft. These procedures often involve forming bone tunnels in the femur and the tibia. Two main categories of procedures for forming the femoral tunnel include a transtibial procedure and a medial portal procedure. In the transtibial procedure, the tibial tunnel can be used to locate the femoral tunnel. While this procedure works for its intended purpose, it is often difficult to position the femoral tunnel entrance at the location of the native ACL footprint. With the medial portal procedure, a guide can be placed through a medial portal rather than the tibial tunnel, which can provide greater freedom to locate the guide relative to the native ACL footprint. While this medial portal procedure also works for its intended purpose, current guide devices, such as with a single plane bend, can require additional manipulation, such as rotation after insertion, as well as may require use of a non-standard medial portal that is "cheated over" toward the medial condyle. Accordingly, there is a need for improvement in the relevant art.

SUMMARY

This section provides a general summary of the disclosure, and is not a comprehensive disclosure of its full scope or all of its features.

In one form, a guide assembly for use in preparing a femur for soft tissue reconstruction is provided in accordance with various aspects of the present disclosure. The guide assembly can include a guide shaft member that can extend from a proximal end to a distal end thereof. The guide shaft member can include a distal region encompassing the distal end. The distal region can have a first bend in a first direction and a second bend in a second direction different than the first direction.

In another form, a guide assembly for use in preparing a femur for soft tissue reconstruction is provided in accordance with various aspects of the present disclosure. The guide assembly can include a cannulated guide shaft member, a cannulated guide member, an alignment member and a cannulated handle. The cannulated guide shaft member can extend from a proximal end to a distal end thereof and can include a first portion extending along a longitudinal axis from the proximal end and a distal region encompassing the distal end. The distal region can have a first bend in a first direction and a second bend in a second direction different than the first direction. The first bend can curve in the first direction along a first plane extending through the first portion and parallel to the longitudinal axis. The second bend can curve in the second direction along a second plane extending perpendicular to the longitudinal axis and the first plane. The cannulated guide member can be coupled to the proximal end of the guide shaft member and can include a first alignment slot extending along a first axis and a second alignment slot extending along a second axis different than the first axis. The alignment member can be configured to be received in one of the first and second alignment slots to provide a visual indication of an orientation of the distal end of the cannulated guide shaft member. A cannulated handle can be coupled to a proximal end of the guide member.

In yet another form, a guide assembly for use in preparing a femur for soft tissue reconstruction is provided in accordance with various aspects of the present disclosure. The guide assembly can include a cannulated guide shaft member, a cannulated guide member, an alignment pin and a cannulated handle. The cannulated guide shaft member can extend from a proximal end to a distal end thereof. The cannulated guide shaft member can include a first portion extending along a longitudinal axis from the proximal end and a distal region encompassing the distal end. The distal region can have a first bend curving in a first direction along a first plane that extends through the first portion and parallel to the longitudinal axis, and a second bend curving in a second direction different than the first direction along a second plane that extends perpendicular to the longitudinal axis and the first plane. The first bend can include an angle between 40 degrees and 50 degrees in the first direction relative to the longitudinal axis and the second bend can include an angle between 20 and 30 degrees in the second direction relative to the longitudinal axis. The cannulated guide member can be coupled to the proximal end of the guide shaft member and can include a first alignment slot extending along a first axis and a second alignment slot extending along a second axis different than the first axis. The first axis can extend parallel to a third plane extending through the first portion and parallel to the longitudinal axis, where the third plane can be perpendicular to the first and second planes. The second axis can extend parallel to an exit trajectory defined by the distal end of the guide shaft member. The alignment pin can be configured to be received in one of the first and second alignment slots to provide a visual indication of an orientation of the distal end of the cannulated guide shaft member. The cannulated handle can be releasably coupled to a proximal end of the guide member.

According to some examples, the first plane can correspond to a sagittal anatomic plane, the second plane can correspond to a coronal anatomic plane, and the third plane can correspond to a transverse anatomic plane. In some examples, the first bend can include an angle of approximately 46 degrees, and the second bend can include an angle of approximately 27 degrees.

According to some examples, at least a portion of the distal region includes both the first bend and the second bend. In one exemplary configuration, the first and second bends can extend along substantially the same portion of the distal region of the guide shaft member. In another exemplary configuration, the distal end of the guide shaft member defines an exit trajectory and the second axis of the second alignment slot can be substantially parallel to the exit trajectory. According to other examples, an offset foot member can be coupled to the distal end of the guide shaft member, where the offset foot member can include a flange with a predetermined offset from the distal end of the guide shaft member when coupled thereto.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 6 is a cross-sectional view of the dual-plane femoral guide assembly of FIG. 5 according to various aspects of the present disclosure;

DETAILED DESCRIPTION

Figure 1:
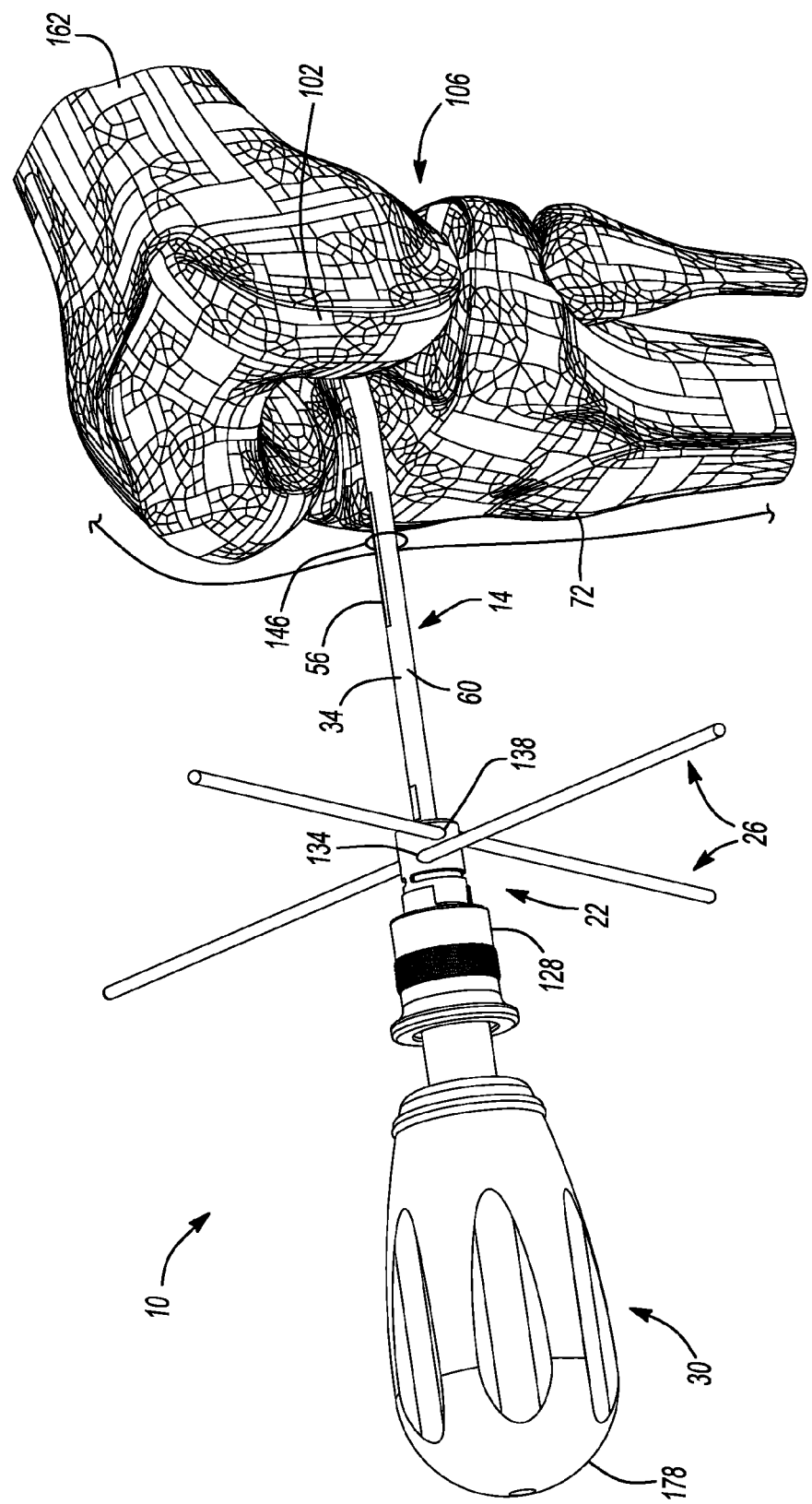
FIG. 1 is a perspective view of an exemplary dual-plane femoral guide assembly shown in an exemplary ACL reconstruction procedure where the guide is positioned through an anteromedial portal according to various aspects of the present disclosure.

The following description is merely exemplary in nature and is not intended to limit the present disclosure, its application, or uses. Although the following description is related generally to methods and apparatus for forming a femoral tunnel in connection with an anterior cruciate ligament (ACL) reconstruction procedure using a medial or anteromedial portal, it should be appreciated that the methods and apparatus discussed herein can be applicable to other ligament reconstruction procedures and/or techniques.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

As briefly discussed above, typical femoral guides for an ACL reconstruction procedure that uses the medial portal technique can include only a single plane bend. As a result, these femoral guides often require manipulation after insertion through the portal, such as rotation, to align with or reach the native ACL footprint, especially more anterior and inferior portions of the footprint. In addition, the medial portal used with the single plane bend guide often has to be "cheated over" toward the medial condyle from the location used for a standard anteromedial portal (e.g., approximately 1 cm medial to the medial edge of the patellar ligament and 1 cm proximal to the proximal surface of the tibial plateau) in an effort to align the distal end of the guide with the native ACL footprint.

Accordingly, the present teachings provide a dual-plane femoral guide assembly for an ACL reconstruction procedure. As will be discussed below, the dual-plane femoral guide assembly of the present teachings includes, among other features, a guide shaft member having the dual-plane or compound bend and a quick-connect guide member having optional alignment member features. In one exemplary configuration, the dual-plane bend can include both a sagittal plane or upward bend and a coronal plane or side-to-side bend.

The dual-plane femoral guide assembly provides for the ability to use the standard anteromedial portal as opposed to the non-standard or "cheated over" anteromedial portal required with the single plane bend guide. Using the standard anteromedial portal can reduce a potential risk of iatrogenic injury to the medial femoral condyle during passage of the guide wire and flexible reamers. In addition, the dual-plane bend of the femoral guide member can eliminate the need to rotate the femoral guide, as well as can facilitate a more perpendicular alignment angle with the femoral lateral notch, which can result in a more circular femoral tunnel opening.

With initial reference to FIGS. 5-8, a dual-plane femoral guide assembly is provided and generally identified at reference numeral 10. As shown, the dual-plane femoral guide assembly 10 can include a curved guide shaft member 14, an optional offset flange or foot member 18, a quick-connect guide member 22, an alignment member 26 and a handle 30. As will be discussed in greater detail below, the dual-plane femoral guide assembly 10 can be provided in kit form where multiple curved guide shaft members are provided with and without various different size offset foot members 18 preassembled thereto. Thus, while the discussion will continue with reference to the illustrated example of the dual-plane femoral guide assembly 10, it will be appreciated that this guide assembly is one version of various guide assembly configurations that can be assembled from the kit that will be discussed below.

In one exemplary configuration, the curved guide shaft member 14 can include a cannulated body 34 extending from a proximal end 38 to a distal end 42. The cannulated body 34 can define a throughbore 46 (FIG. 6) extending from the proximal end 38 to the distal end 42. It should be appreciated that while the discussion will continue with reference to the curved guide shaft member 14 including a cannulated body 34, other body forms can be utilized such as a tube having a slot extending along a length of the tube. In the exemplary configuration shown in the various figures, the cannulated body 34 can have a circular or substantially circular shape in cross-section. The cannulated body 34 can also include a top or upward/superior side 48 and an opposite or bottom/inferior side 52. The superior side 48 can include a visually observable marking 56, as shown for example in FIGS. 5 and 6. The proximal end 38 of the curved guide shaft member 14 can be coupled to the quick-connect guide member 22, as will be discussed in greater detail below. The distal end 42 of the curved guide shaft member 14 can include a cut-out or window 58 configured to provide visual access to a guide pin or wire movably positioned in curved guide shaft member 14, as will also be discussed in more detail below.

Figure 7A:
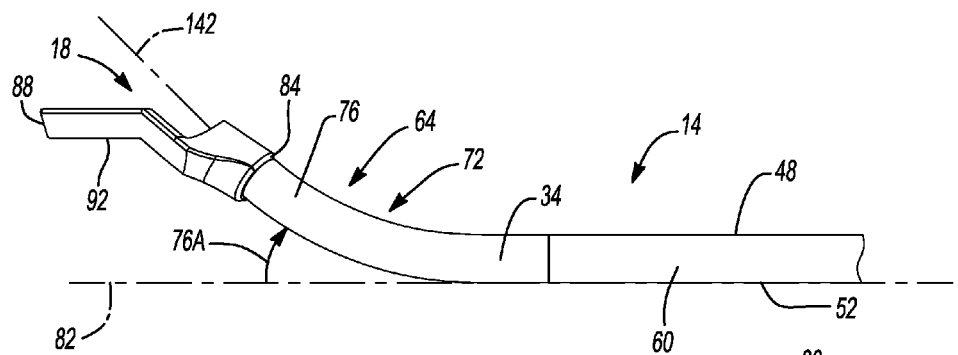
FIG. 7A is a partial side view of a guide shaft member of the dual-plane femoral guide assembly according to various aspects of the present disclosure.
Figure 7B:
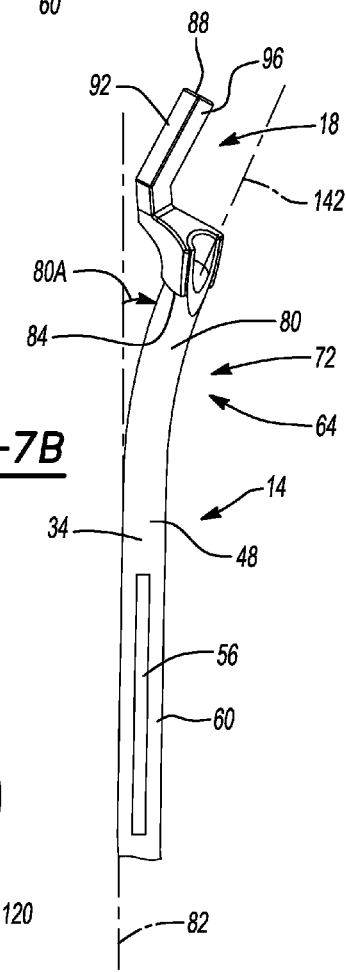
FIG. 7B is a partial top view of the guide shaft member of the dual-plane femoral guide assembly according to various aspects of the present disclosure.
Figure 8:
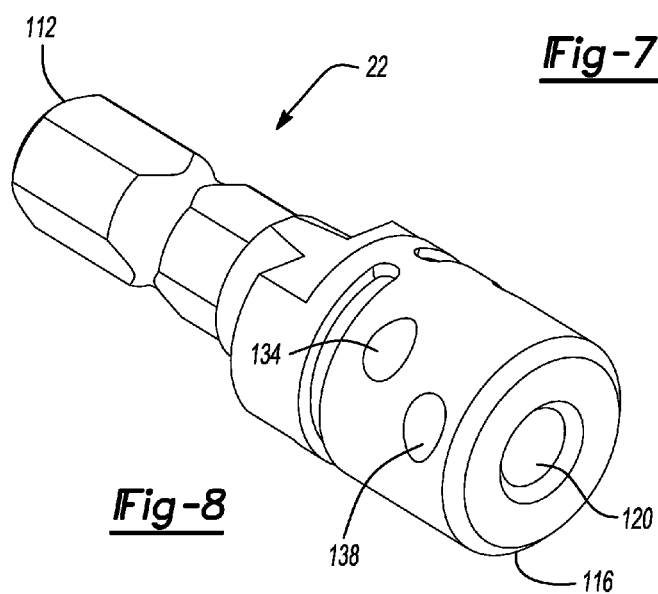
FIG. 8 is a perspective view of a quick-connect guide member of the dual-plane femoral guide assembly according to various aspects of the present disclosure.

The curved guide shaft member 14 can include a straight or linear portion 60 and a curved portion having a dual-plane bend 64, as briefly discussed above. The straight portion 60 can extend from the proximal end 38 to an intermediate region 68 between the proximal and distal ends 38, 42. The dual-plane bend 64 can be formed in a distal region 72 of the curved guide shaft member 14 that extends from the intermediate region 68 to and includes the distal end 42. In one exemplary configuration, the dual-plane bend 64 can include both a first bend 76 and a second bend 80, each relative to a longitudinal axis 82 of the straight portion 60, as best shown in FIGS. 7A-7B. As can be seen in the figures, at least a portion of the curved distal region 72 can include both the first and second bends 76, 80. In one exemplary configuration, the first and second bends 76, 80 can extend along or substantially along the distal region or the same portion of the distal region. The first bend 76 can be a sagittal plane or upward bend and the second bend 80 can be a coronal plane or side-to-side bend, as best shown in FIGS. 7A-7B.

Figure 2:
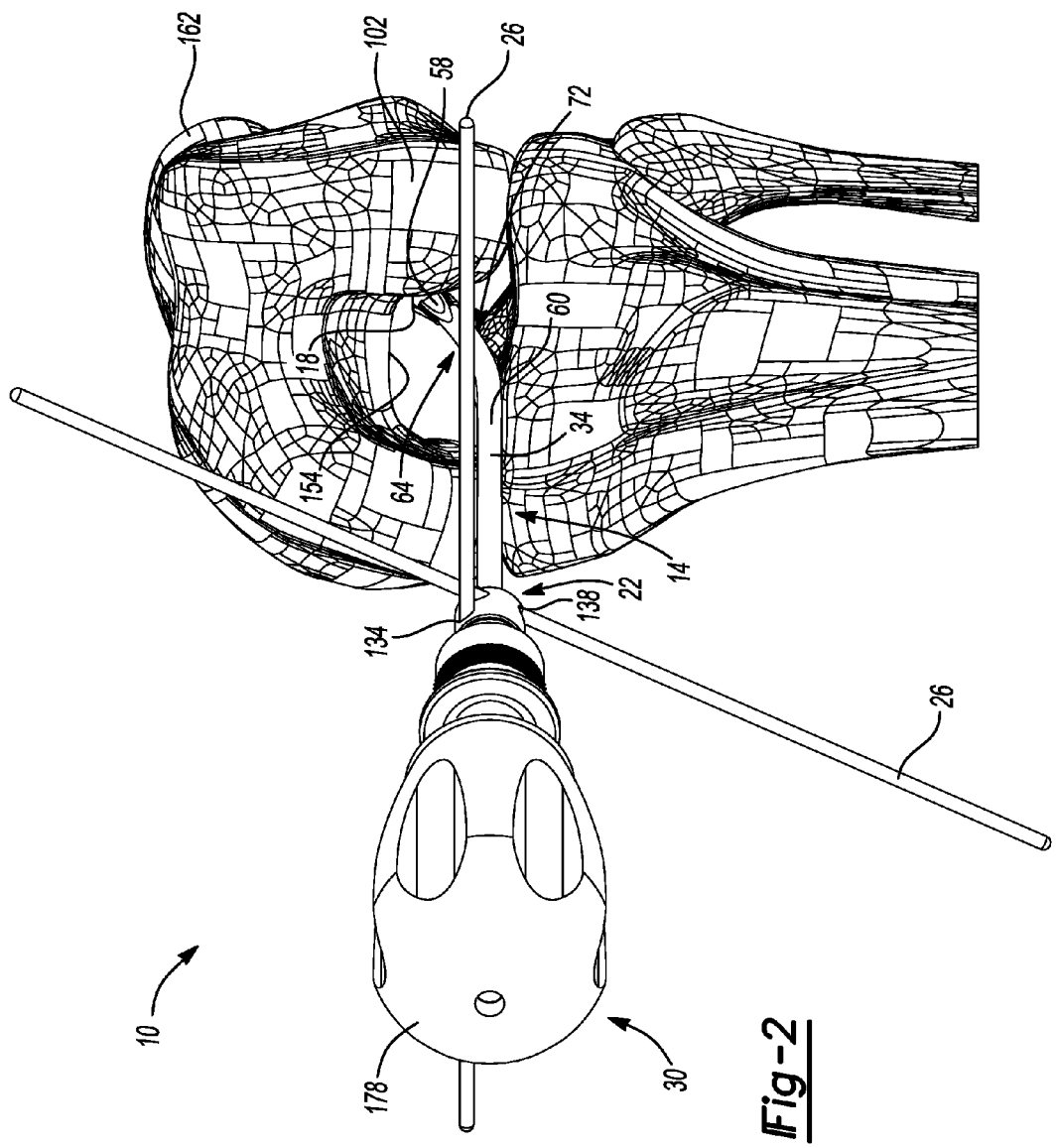
FIG. 2 is another view of the dual-plane femoral guide assembly and exemplary ACL reconstruction procedure using the anteromedial portal according to various aspects of the present disclosure.
Figure 3:
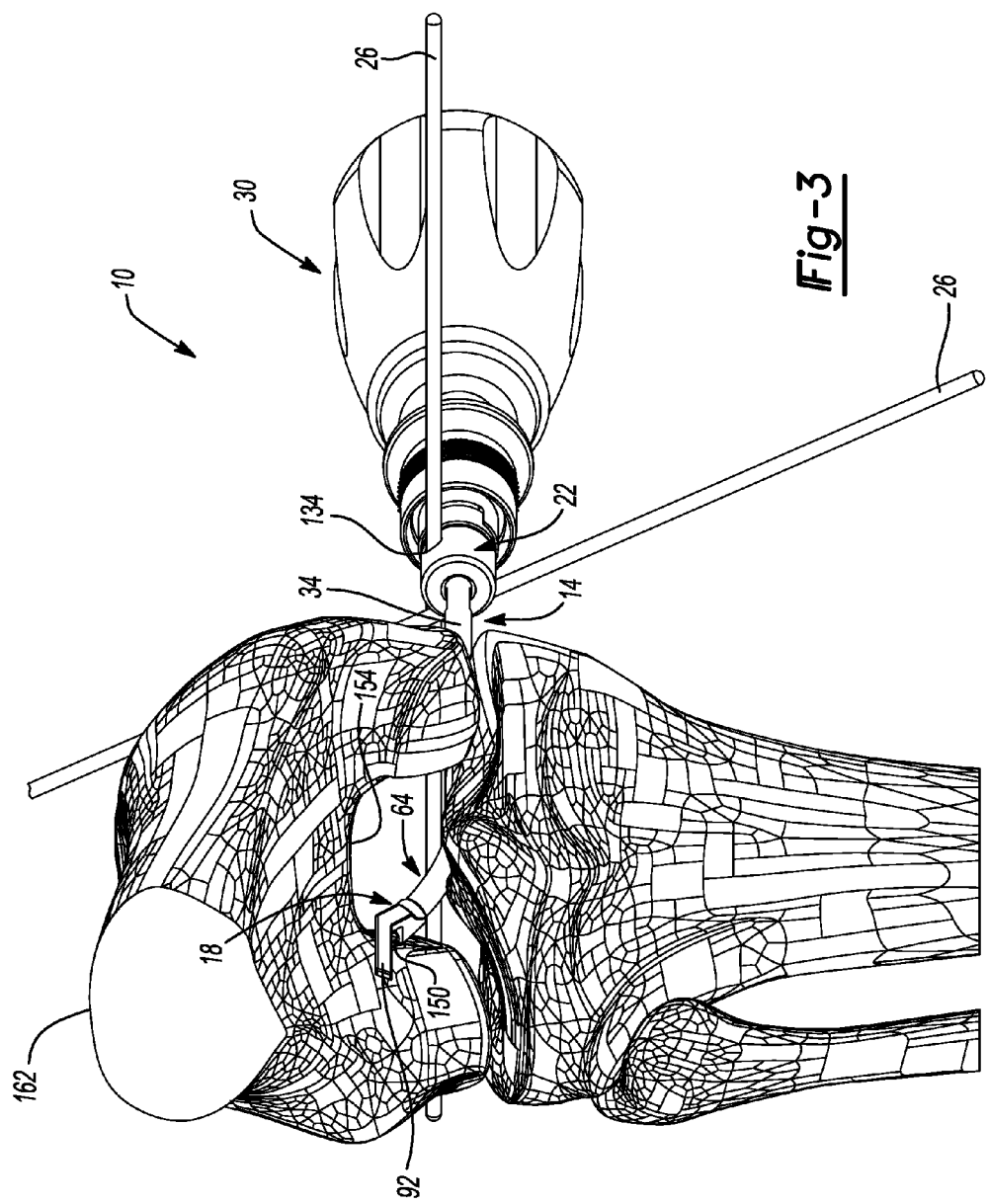
FIG. 3 is another view of the dual-plane femoral guide assembly and exemplary ACL reconstruction procedure using the anteromedial portal according to various aspects of the present disclosure.

For purposes of discussion only, the dual-plane bend 64 will be described below with specific reference to the sagittal, coronal and transverse anatomical planes known to those skilled in the art. In this regard, to establish a frame of reference, the straight or substantially straight portion 60 of the curved guide shaft member 14 is positioned parallel to the transverse and sagittal planes with the marking 56 (and thus the top side 48) positioned facing upward or in a superior direction. In this frame of reference, the coronal plane extends through the straight portion and perpendicular to the longitudinal axis 82 and both the sagittal and transverse planes. With this frame of reference, the first bend 76 can be along the sagittal plane in an upward or superior direction and the second bend 80 can be along the coronal plane in a sideways direction, as shown for example in FIGS. 7A-7B with reference to FIGS. 1-3.

The dual-plane bend 64 can provide the various advantages or benefits discussed above and can be formed at various angles relative to the longitudinal axis 82 of the straight portion 60 of cannulated body 34. In one exemplary configuration, the first or sagittal plane bend 76 can be at an angle 76A of approximately 40 to 50 degrees, including 42 to 45 degrees and approximately 46 degrees, as shown in FIG. 7A. The second or coronal plane bend 80 can be at an angle 80A of approximately 20 to 30 degrees, including approximately 27 degrees, as shown in FIG. 7B.

The curved guide shaft member 14 can also be provided in various versions, including a version with offset foot member 18 coupled or assembled to the distal end 42, and a version without the offset foot member 18. The offset foot member 18 can include a proximal end 84 and a distal end 88. The proximal end 84 can be configured for coupling to the distal end 42 of curved guide shaft member 14. For versions of the curved guide shaft member 14 that include the offset foot member 18, the offset foot member 18 can be preassembled thereto. In one exemplary configuration, the offset foot member 18 can be integrally formed with this version of the curved guide shaft member 14. The distal end 88 of the offset foot member 18 can be formed by an offset flange member 92.

The offset flange member 92 can be offset by various different amounts and thus the offset foot member 18 can be provided in various different sizes each having a different offset amount from an axis or trajectory, such as an exit trajectory 142 (FIGS. 4 and 5) of the distal end 42 of the cannulated body member 34. In addition, a surface 96 (FIG. 4A) of the offset flange member 92 that is configured to engage tissue can be provided in various different shapes. The offset foot member 18 can be optionally used and can engage a portion of a lateral femoral condyle 102 of a knee joint 106, as shown for example in FIG. 1 with reference to FIG. 3. Those skilled in the art will appreciate that a certain size offset foot member 18 can be optionally selected based on surgeon preferences in connection with a patient's anatomy to achieve a desired amount of bone wall thickness and can be a function of graft size (e.g., a smaller graft size can correspond to a smaller offset amount).

Figure 5:
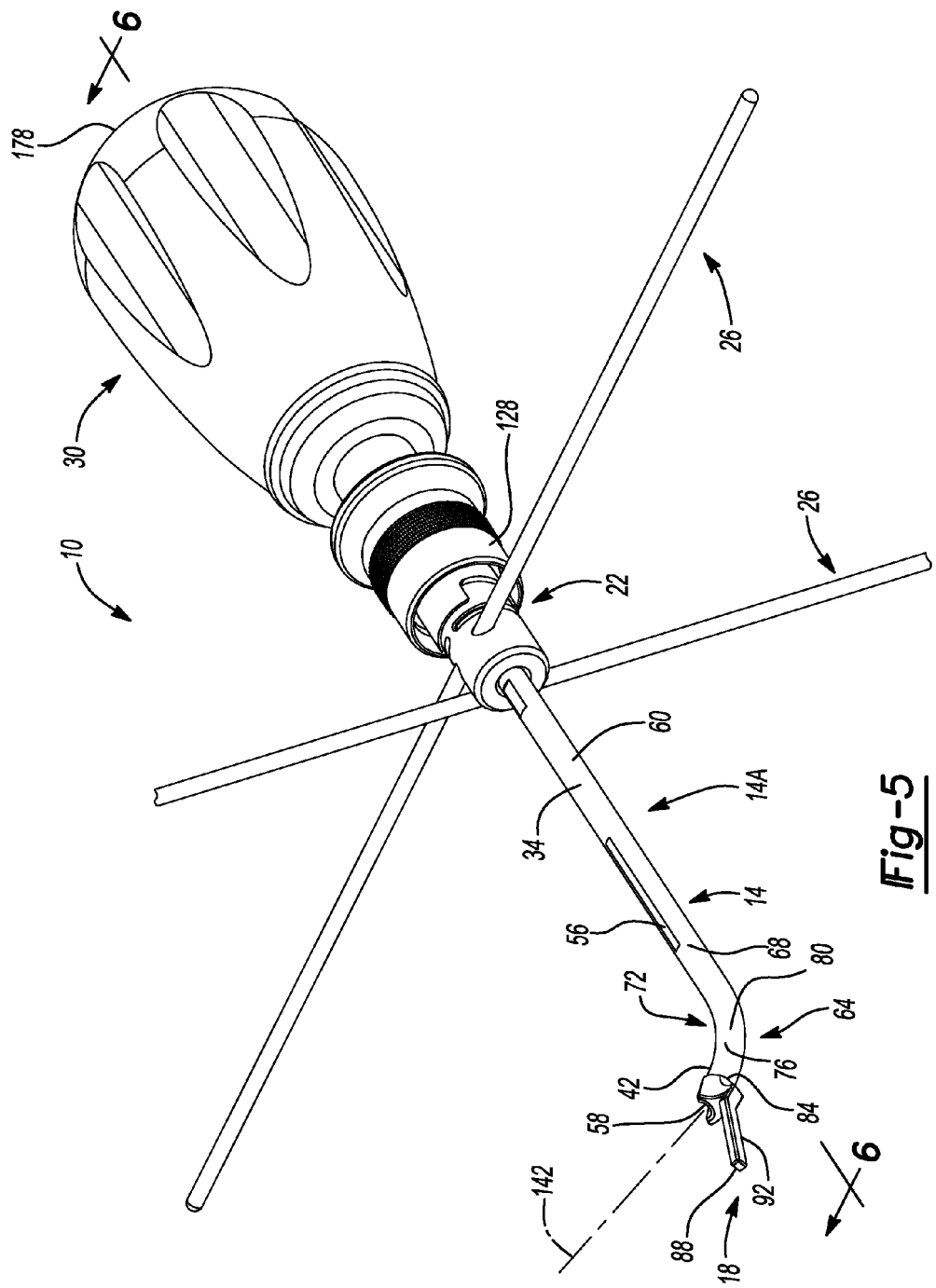
FIG. 5 is a perspective view of the dual-plane femoral guide assembly showing optional alignment member orientations according to various aspects of the present disclosure.
Figure 5A:
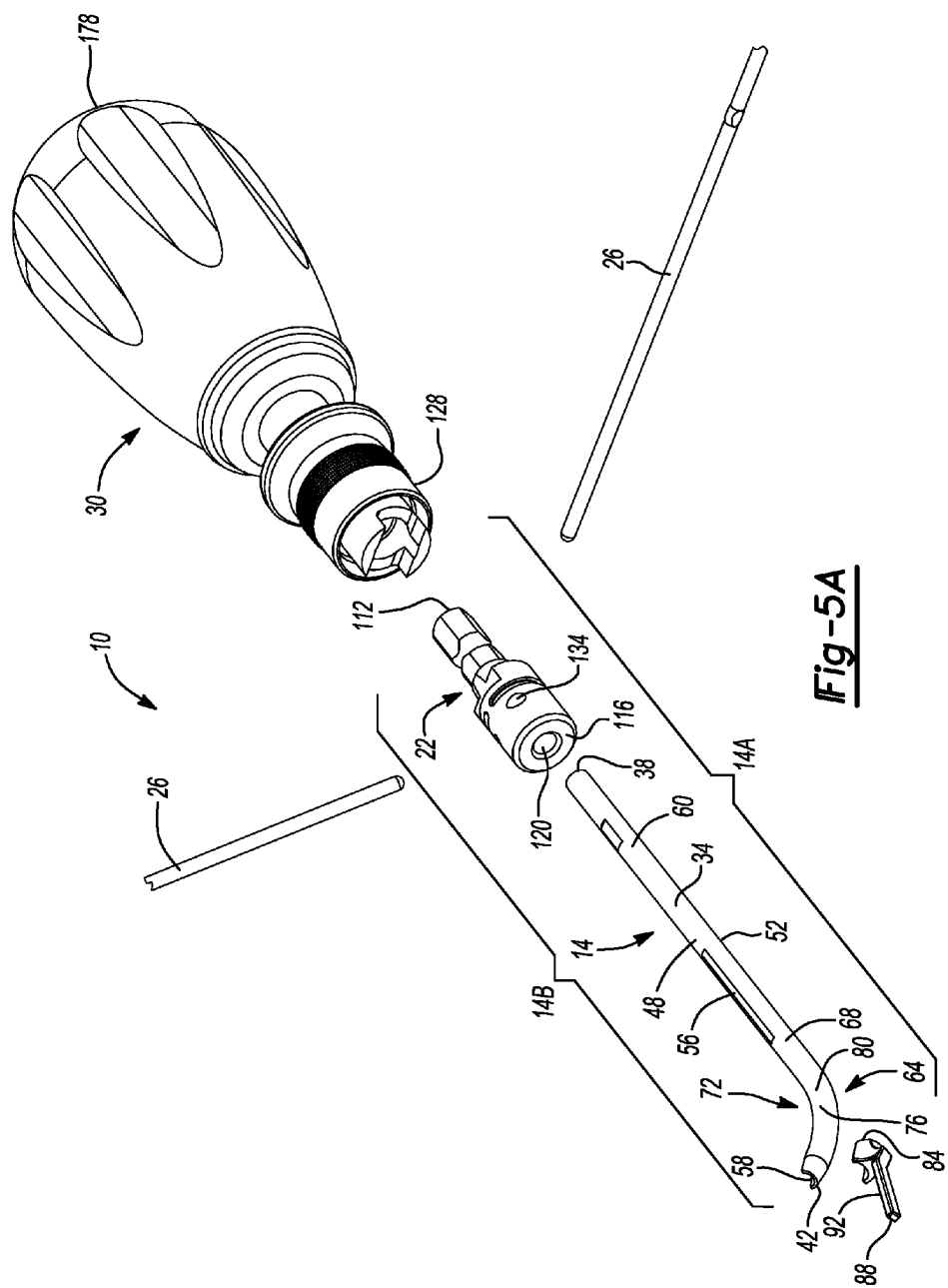
FIG. 5A is an exploded perspective view of the dual-plane femoral guide assembly of FIG. 5 according to various aspects of the present disclosure.

The quick-connect guide member 22 can include a proximal end 112 and a distal end 116. The distal end 116 can define a connection site 120 for coupling to the proximal end 38 of curved guide shaft member 14, as shown for example in FIG. 8 and FIG. 5A with reference to FIG. 5. The proximal end 112 of quick-connect guide member 22 can be releasably coupled to a distal end 128 of handle 30. In the exemplary configuration illustrated, the proximal end 112 can be releasably coupled to the distal end 128 of handle 30 with a "Hudson-style" quick-connection.

Quick-connect guide member 22 can define first and second alignment apertures or slots 134, 138 configured to receive the alignment member 26. It will be appreciated that while the certain figures illustrate two alignment members, only one alignment member may be provided (e.g., with the kit) for use with either of the alignment slots 134, 138. In the exemplary configuration illustrated, the alignment member 26 can be an alignment pin. As will be discussed in greater detail below, the alignment pin 26 can be positioned through either of the slots 134, 138 to provide a visual reference to the surgeon as to the orientation of the distal end 42 of the curved guide shaft member 14.

Briefly, however, the first alignment slot 134 can be a horizontal coronal alignment slot for use in aligning the alignment pin 26 received therethrough parallel to a joint line or condylar axis of the knee joint 106. The second alignment slot 138 can be a trajectory alignment slot positioned at an acute angle relative to the first alignment slot 134 and parallel to the exit trajectory axis or orientation 142 of the distal end 42 of curved guide shaft member 14, as shown for example in FIGS. 2 and 3. In this regard, trajectory alignment slot 138 can be used to visually indicate or predict where the guide wire/pin positioned through curved guide shaft member 14 will exit the lateral cortex, as shown for example in FIG. 4.

The quick-connect guide member 22 can be assembled to the curved guide shaft member 14 such that the dual-plane bend 64 can be at a predetermined fixed orientation relative to quick-connect guide member 22. For example, and using the anatomical plane frame of reference discussed above, the first or horizontal alignment slot 134 can be parallel to or substantially parallel to the transverse plane when the straight portion 60 of cannulated body 34 is parallel to the transverse plane. With this frame of reference, the horizontal alignment slot 134 can also be perpendicular to the sagittal plane.

As briefly discussed above, the illustrated dual-plane femoral guide assembly 10 can be provided as part of or in the form of a kit. In one exemplary configuration, the kit can include a plurality of curved guide shaft members 14 each with a different size offset foot member 18 preassembled thereto, and one curved guide shaft member 14 without an offset foot member 18 for both a left knee joint and a right knee joint. In this exemplary configuration, the different size offset foot members 18 for each knee joint can include offset foot members 18 having 4.0, 5.0, 6.0 and 7.0 mm offsets. Each of the curved guide shaft members 14 included in the kit can also be preassembled to a quick-connect guide member 22 in the manner discussed above. The curved guide shaft members 14 provided in the kit and preassembled with one of the four sizes of offset foot members 18 and the quick-connect guide member 22 can be referred to hereinafter as a curved guide shaft member sub-assembly 14A. The curved guide shaft member 14 provided in the kit and preassembled with only the quick-connect guide member 22 can be referred to hereinafter as a curved guide shaft member sub-assembly 14B. One handle 30 and the alignment pin 26 configured for use with any of the sub-assemblies 14A and 14B can also be provided in the kit.

In operation, the surgeon can select a desired curved guide shaft member sub-assembly 14A having the desired size offset foot member 18 or a curved guide shaft member sub-assembly 14B without the offset foot member 18. The selected and assembled sub-assembly 14A or 14B can be releasable coupled to handle 30. The selected dual-plane femoral guide assembly 10 can then be positioned through a standard anteromedial portal 146 (FIG. 1) and aligned with the native footprint 150 of the ACL in the femoral notch 154 of femur 162, as shown for example in FIGS. 2-4. The superior marking 56, such as a laser etched line, can aid the surgeon in maintaining a desired orientation of the guide assembly 10. For example, in a typical operating room environment, the superior marking 56 should be facing upward (e.g., facing the ceiling of the operating room).

The surgeon can optionally use alignment pin 26 in either of the alignment slots 134, 138 to aid in the coronal and/or trajectory alignment of the curved guide shaft member 14. For example and with reference to FIGS. 1-4, alignment pin 26 may be placed in horizontal alignment slot 134 and the guide assembly 10 can be orientated such that alignment pin 26 is orientated parallel to the condylar axis or joint line of knee joint 106, as shown for example in FIGS. 1-3. The alignment pin 26 may also be placed in the diagonal or trajectory alignment slot 138 and the guide assembly 10 can be orientated such that alignment pin 26 can visually predict the axis of the femoral tunnel and where it will exit the femur 162, as shown for example in FIG. 4.

Figure 4:
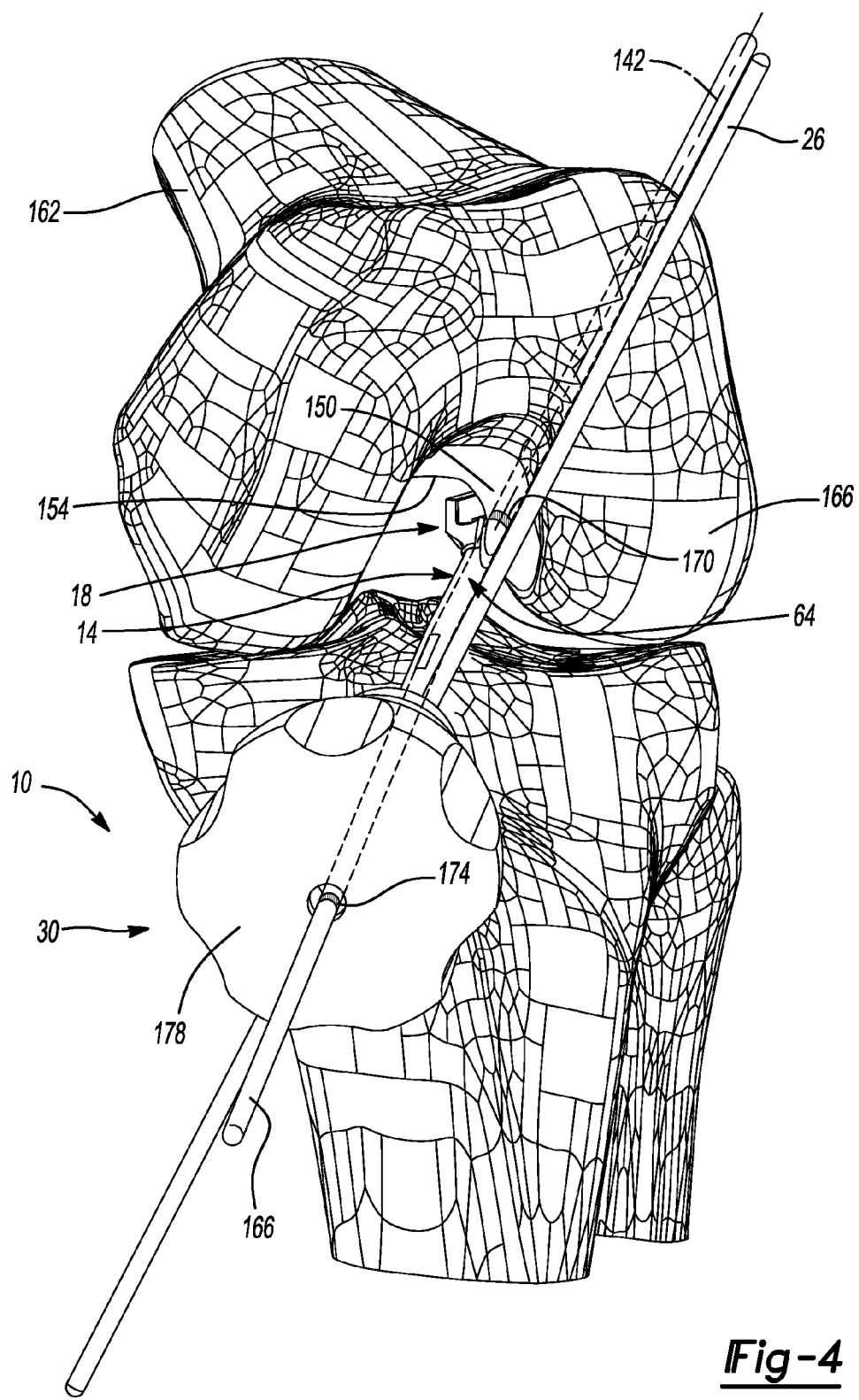
FIG. 4 is a view of the dual-plane femoral guide assembly using a trajectory alignment member in the exemplary ACL reconstruction procedure according to various aspects of the present disclosure.
Figure 4A:
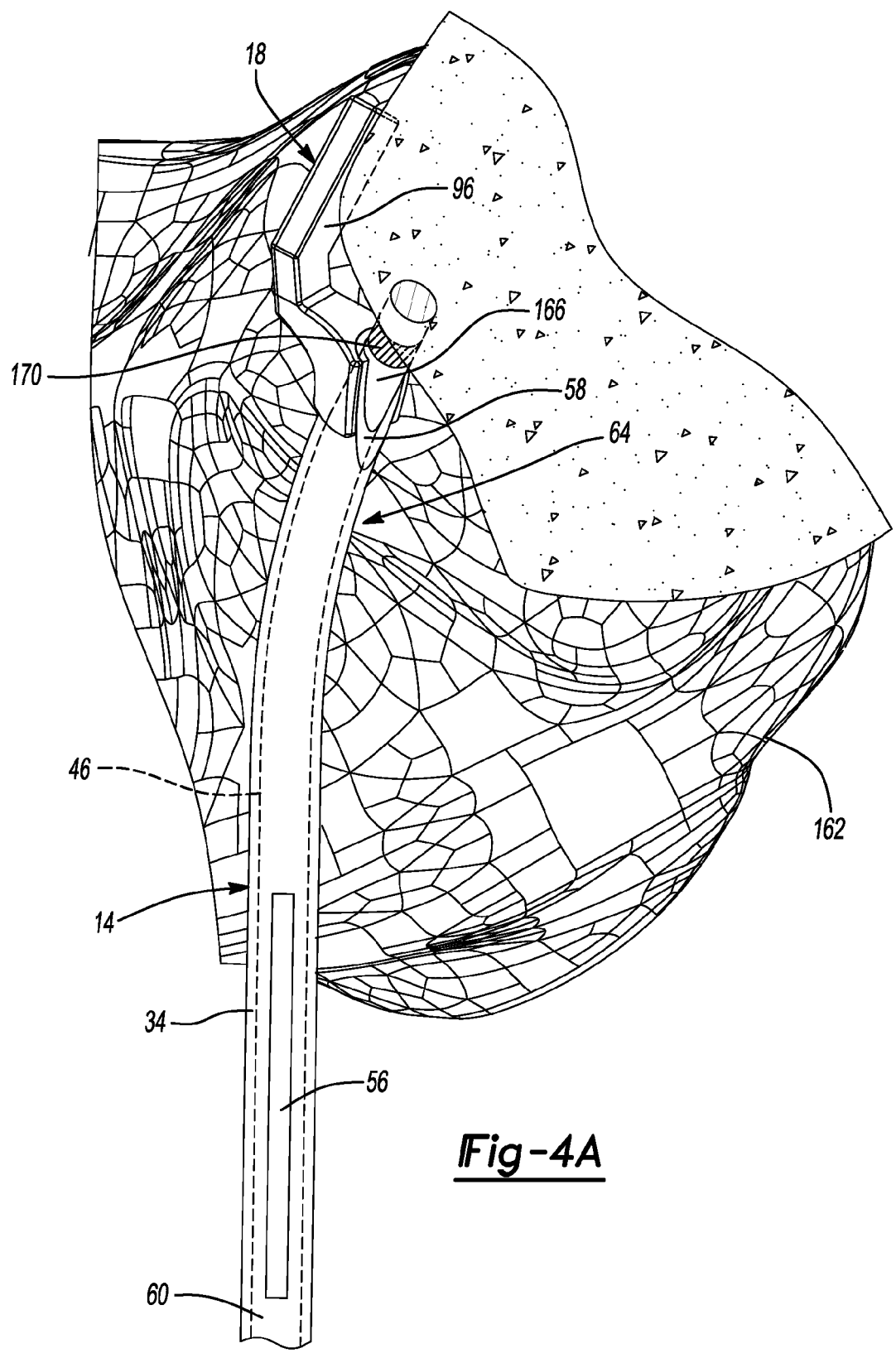
FIG. 4A is a view of a distal end of the dual-plane femoral guide assembly showing a sight window and an exemplary guide wire according to various aspects of the present disclosure.

With the dual-plane femoral guide assembly 10 in the desired position, a flexible guide pin or wire 166 can be positioned into the cannulated body member 34 via the cannulated handle 30. The flexible guide pin 166 can be advanced under power, such as via a pin driver, into the femur 162. The flexible guide pin 166 can be visualized through the window 58 at the distal end 42 of curved guide shaft member 14, as generally shown in FIG. 4A. The flexible guide pin 166 can be advanced until it exits the femur 162 and protrudes through the skin on the lateral side of the thigh and an optional marking 170 on the flexible guide pin 166 can be visualized in the window 58, as shown in FIGS. 4 and 4A. For additional reference, an additional marking 174 on the flexible guide pin 166 can be positioned at a proximal end 178 or entrance to handle 30, as also shown in FIG. 4. With the flexible guide pin 166 in place, the dual-plane femoral guide assembly 10 can be removed and a cannulated flexible reamer corresponding to a diameter of the graft can be positioned over flexible guide wire 166 and used to ream a socket in the femur 162 for receipt of the graft.

While one or more specific examples or aspects have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A guide assembly for use in preparing a femur for soft tissue reconstruction, comprising:

a guide shaft member extending from a proximal end to a distal end, the guide shaft member including:
a distal region encompassing the distal end, the distal region having a first bend in a first direction and a second bend in a second direction different than the first direction, and
a first portion extending from the proximal end to the distal region along a longitudinal axis, the first bend curving in the first direction along a first plane extending through the first portion and parallel to the longitudinal axis, the second bend curving in the second direction along a second plane extending perpendicular to the longitudinal axis and the first plane;

a guide member coupled to the proximal end of the guide shaft member and including at least one of a first alignment slot extending along a first axis and a second alignment slot extending along a second axis different than the first axis, the first axis of the first alignment slot being parallel to a third plane that extends through the first portion and perpendicular to the first and second planes; and an alignment member configured to be received in one of the first alignment slot and the second alignment slot to provide a visual indication of an orientation of a distal end of the cannulated guide shaft member.

2. The guide assembly of claim 1, wherein the first plane corresponds to a sagittal anatomic plane and the second plane corresponds to a coronal anatomic plane.

3. The guide assembly of claim 2, wherein the guide shaft member includes a cannulated guide shaft member.

4. The guide assembly of claim 1, wherein the third plane corresponds to a transverse anatomic plane.

5. The guide assembly of claim 1, wherein the first bend includes an angle between 40 degrees and 50 degrees in the first direction relative to the longitudinal axis.

6. The guide assembly of claim 5, wherein the second bend includes an angle between 20 and 30 degrees in the second direction relative to the longitudinal axis.

7. The guide assembly of claim 6, wherein the second bend includes an angle of approximately 27 degrees in the second direction relative to the longitudinal axis.

8. The guide assembly of claim 6, wherein at least a portion of the distal region includes both the first bend and the second bend.

9. The guide assembly of claim 6, wherein the first and second bends extend along substantially the same portion of the distal region of the guide shaft member.

10. The guide assembly of claim 6, wherein the distal end of the guide shaft member defines an exit trajectory and wherein the second axis of the second alignment slot is substantially parallel to the exit trajectory.

11. The guide assembly of claim 10, wherein the second axis is orientated at an acute angle to the first axis.

12. The guide assembly of claim 11, wherein the alignment member includes an alignment pin, wherein the alignment pin, when positioned in the first alignment slot, is adapted to be aligned parallel to a condylar axis of a knee joint, and wherein the alignment pin, when placed in the second alignment slot, is adapted to visually indicate a trajectory of a femoral tunnel.

13. The guide assembly of claim 1, wherein the first bend includes an angle of approximately 46 degrees in the first direction relative to the longitudinal axis.

14. The guide assembly of claim 1, further comprising:
an offset foot member coupled to the distal end of the guide shaft member, the offset foot member including a flange with a predetermined offset from the distal end of the guide shaft member when coupled thereto; and
a cannulated handle, the handle configured to be releasable coupled to a proximal end of the guide member.

15. A guide assembly for use in preparing a femur for soft tissue reconstruction, comprising:
a cannulated guide shaft member extending from a proximal end to a distal end, the cannulated guide shaft member including a first portion extending along a longitudinal axis from the proximal end and a distal region encompassing the distal end, the distal region having a first bend in a first direction and a second bend in a second direction different than the first direction, the first bend curving in the first direction along a first plane extending through the first portion and parallel to the longitudinal axis, the second bend curving in the second direction along a second plane extending perpendicular to the longitudinal axis and the first plane;
a cannulated guide member coupled to the proximal end of the guide shaft member and including at least one of a first alignment slot extending along a first axis and a second alignment slot extending along a second axis different than the first axis;
an alignment member configured to be received in one of the first and second alignment slots to provide a visual indication of an orientation of the distal end of the cannulated guide shaft member; and
a cannulated handle coupled to a proximal end of the guide member.

16. The guide assembly of claim 15, wherein the first axis of the first alignment slot extends parallel to a third plane extending through the first portion and parallel to the longitudinal axis, the third plane being perpendicular to the first and second planes.

17. The guide assembly of claim 16, wherein the first plane corresponds to a sagittal anatomic plane, the second plane corresponds to a coronal anatomic plane, and the third plane corresponds to a transverse anatomic plane.

18. The guide assembly of claim 17, wherein the first bend includes an angle between 40 degrees and 50 degrees in the first direction relative to the longitudinal axis and the second bend includes an angle between 20 and 30 degrees in the second direction relative to the longitudinal axis.

19. The guide assembly of claim 17, wherein the first bend includes an angle of approximately 46 degrees and the second bend includes an angle of approximately 27 degrees.

20. The guide assembly of claim 17, wherein at least a portion of the distal region includes both the first bend and the second bend.

21. The guide assembly of claim 15, wherein the distal end of the guide shaft member defines an exit trajectory and wherein the second axis of the second alignment slot is substantially parallel to the exit trajectory.

22. The guide assembly of claim 15, further comprising an offset foot member coupled to the distal end of the guide shaft member, the offset foot member including a flange with a predetermined offset from the distal end of the guide shaft member when coupled thereto.

23. A guide assembly for use in preparing a femur for soft tissue reconstruction, comprising:
a cannulated guide shaft member extending from a proximal end to a distal end, the cannulated guide shaft member including a first portion extending along a longitudinal axis from the proximal end and a distal region encompassing the distal end, the distal region having:
a first bend curving in a first direction along a first plane extending through the first portion and parallel to the longitudinal axis, and
a second bend curving in a second direction different than the first direction along a second plane extending perpendicular to the longitudinal axis and the first plane,
wherein the first bend includes an angle between 40 degrees and 50 degrees in the first direction relative to the longitudinal axis and the second bend includes an angle between 20 and 30 degrees in the second direction relative to the longitudinal axis;
a cannulated guide member coupled to the proximal end of the guide shaft member and including at least one of a first alignment slot extending along a first axis and a second alignment slot extending along a second axis different than the first axis, the first axis extending parallel to a third plane extending through the first portion and parallel to the longitudinal axis, the third plane being perpendicular to the first and second planes, the second axis extending parallel to an exit trajectory defined by the distal end of the guide shaft member;
an alignment pin configured to be received in one of the first and second alignment slots and provide a visual indication of an orientation of the distal end of the cannulated guide shaft member; and
a cannulated handle releasably coupled to a proximal end of the guide member.

\* \* \* \* \*

UNITED STATES PATENT AND TRADEMARK OFFICE
CERTIFICATE OF CORRECTION

PATENT NO. : 9,192,401 B2
APPLICATION NO. : 14/018973
DATED : November 24, 2015
INVENTOR(S) : Harbison et al.

Page 1 of 1

It is certified that error appears in the above-identified patent and that said Letters Patent is hereby corrected as shown below:

IN THE CLAIMS

In column 9, line 1, in Claim 3, after "claim 2,", delete "¶", therefor

Signed and Sealed this
Fifth Day of April, 2016

Michelle K. Lee
*Director of the United States Patent and Trademark Office*